United States Patent [19]

McKenna

[11] Patent Number: 5,499,415
[45] Date of Patent: Mar. 19, 1996

[54] STABILIZED, CANTILEVERED, PATIENT TRAUMA TABLE SYSTEM

[75] Inventor: Gilbert W. McKenna, Revere, Mass.

[73] Assignee: Analogic Corporation, Peabody, Mass.

[21] Appl. No.: 193,782

[22] Filed: Feb. 8, 1994

[51] Int. Cl.⁶ .................................................. A61B 6/04
[52] U.S. Cl. ................................................ 5/601; 328/209
[58] Field of Search ..................... 5/601, 611; 378/209; 108/109

[56] References Cited

U.S. PATENT DOCUMENTS

| | | | |
|---|---|---|---|
| 4,475,072 | 10/1984 | Schwehr et al. | 5/601 X |
| 4,613,122 | 9/1986 | Manabe | 5/611 X |
| 4,727,328 | 2/1988 | Carper et al. | 328/209 X |
| 4,773,637 | 9/1988 | Jarin | 5/601 X |
| 4,914,682 | 4/1990 | Blumenthal | 378/209 X |
| 4,944,501 | 6/1990 | Sireul et al. | 5/601 |
| 4,984,774 | 1/1991 | Zupancic et al. | 5/601 |
| 5,273,043 | 12/1993 | Ruike | 378/201 X |

FOREIGN PATENT DOCUMENTS

WO87/04609  8/1987  Japan .

*Primary Examiner*—Michael F. Trettel
*Attorney, Agent, or Firm*—Lappin & Kusmer

[57] ABSTRACT

A patient trauma table is described which is adapted for use with medical imaging systems so that the patient can be easily positioned in the imaging system without the necessity of transferring the patient to a special table, making the table extremely useful for supporting a patient during emergency or surgical intervention. The patient trauma table has an elongated top patient-supporting panel capable of being moved into a cantilevered relation to the table base so that a portion of the panel is disposed in an imaging position with respect to the medical imaging equipment. A system for stabilizing the patient supporting panel preferably includes means for releasably locking the table to the imaging equipment to fix the imaging position; and stabilizing support assembly including a support arm having a roller at one end and mounted on the medical imaging equipment so that the roller can be incrementally, vertically moved into and out of contact with the underside of the cantilevered end of the table panel. For safety reasons, a sensor, preferably in the form of a strain gauge, is coupled to the support arm so as to provide an output signal that will stop the advancement of the support arm further against the top when a predetermined roller contact force is exceeded. A counter is provided for counting the steps provided by the stepper motor driving the support arm so that the precise position of the table top with respect to the components of the imaging equipment can be determined.

20 Claims, 5 Drawing Sheets

STABILIZED, CANTILEVERED, PATIENT TRAUMA TABLE SYSTEM

RELATED APPLICATIONS

This application is related to U.S. patent application Ser. No. 08/193,783, filed in the name of Gilbert W. McKenna and entitled "X-ray Tomographic Scanning System", now abandoned in favor of copending U.S. patent application Ser. No. 08/359,845 filed Dec. 20, 1994, now U.S. Pat. No. 5,473,657 as a continuation of application Ser. No. 08/193,783, U.S. patent application Ser. No. 08/193,696, now abandoned, filed in the name of Gilbert W. McKenna and Ronald E. Swain and entitled "Tomographic Scanner Having Center of Rotation for all Physics" (Attorney's Docket No. ANA-31), now abandoned in favor of copending U.S. patent application Ser. No. 08/351,880 filed Dec. 8, 1994, now U.S. Pat. No. 5,448,608, as a continuation of application Ser. No. 08/193,696 and U.S. patent application Ser. No. 08/193,562, now U.S. Pat. No. 5,448,607 name of Gilbert W. McKenna and entitled "X-ray Tomography System with Gantry Pivot and Translation Control", all filed simultaneously herewith and assigned to the present assignee.

FIELD OF THE INVENTION

The present invention relates to medical imaging systems, and more particularly to an improved, stabilized, cantilevered, patient trauma table for use in such a system.

BACKGROUND, OBJECTS AND SUMMARY OF THE INVENTION

Patient tables, particularly gurneys, are ubiquitous throughout hospitals. Gurneys are well known for transporting patients and useful for a variety of specialized tasks. For example, gurneys have been used to receive traumatized patients in emergency situations, transport patients from one location to another, as well as serve as operating tables during surgery. In some cases certain medical imaging equipment, such as ultrasound units can be used on patients lying on gurneys without moving the patient, because in such cases the imaging equipment is readily positionable with respect to the patient.

Larger imaging equipment, such as CT, MRI and PET scan systems, however, are usually too large to move relative to a patient. A CT scan system, for example, includes supporting structure, usually in the form of a yoke, for supporting a gantry. The latter includes a frame, which in turn supports a centrally apertured disk for rotation relative to the frame about a rotation axis. Imaging equipment is mounted on the disk so as to rotate with the disk about its center aperture. The imaging equipment includes an X-ray source which may provide periodic pulses or continuous wave radiation. In third generation CT scan machines, X-rays are detected by a detector array mounted on the disk diametrically across from the source, while in fourth generation machines X-rays emitted by the source are detected by a plurality of detectors fixed circumferentially around the frame. In both types of machines the detectors are positioned and aligned with respect to the source so that the ray paths of the X-rays generated by the source and subsequently sensed by the detectors are all disposed within a common mean scanning plane (perpendicular to the axis of rotation of the disk).

A patient must be positioned through the central aperture of the disk so that the scanning plane passes through a select part of the patient for which an image is to be formed. This arrangement provides information corresponding to variations in X-ray absorption measured by the detectors during rotation of the disk about the patient. Upon known (Radon) mathematical processing of the information, visual images can be "back projected", each representing density distribution of a slice along the scanning plane, through the part of the patient positioned in the plane between the source and detectors.

The formation of a meaningful image depends, inter alia, upon the pertinent part of the patient being positioned within the central aperture of the disk and remaining immobile in that position during scanning. The quality of the data also critically depends upon (1) the imaging components (i.e., the source, and in the case of third generation machines also the detectors) positioned on the disk moving through a smooth circular path about a common point during a scan, i.e., the image "center", or "isocenter" (which should be coincident with the axis of the disk), and (2) the image center remaining fixed relative to the patient so that no relative, lateral movement occurs between the patient and the imaging components. Since even minor relative lateral movement between the patient and the imaging components within the scanning plane during a scan can cause errors resulting in faulty or erroneous images, such apparatus has been provided as massively reinforced devices often weighing a ton or more.

MRI and PET equipment exhibits many similar characteristics, particularly being large and heavy because such equipment employs large magnets. As a result such massive devices are not readily manipulable to adjust the location of the disk aperture to the position of the patient. In addition, since imaging requires the proper positioning of the patient within the equipment, the table upon which the patient rests must usually be translated in a direction parallel to the axis of the imaging components. Accordingly, such equipment is typically provided with its own table coupled to the scanning equipment such that the table moves through the center aperture so as to properly position the patient so that the patient can be scanned.

Too often, however, a patient who is in need of a scan is usually reposed on a gurney, or other type of patient table, in a traumatized state, because, for example, of an injury or because he or she is having surgery performed. In such cases it is necessary to transfer the patient from the gurney to the table of the scanner which can exacerbate the trauma and cause harm to the patient. This is particularly a problem in surgery, for example, where a surgeon may want to know whether he or she has completely removed cancerous tissue, or is entering the brain at a prescribed location. Under such circumstances it would be necessary to suture the patient to move him or her to the location of a CT scanner, move the patient off the gurney to the scan table, perform the scan, move the patient back to the gurney, and then move the patient back to the operating room if further surgical intervention is warranted. Because of the possible trauma that can result from such patient movement during such surgery, such scans are usually not performed.

Accordingly, at least one object of the present invention is to provide a patient trauma table, preferably in the form of a gurney, which can support a traumatized patient and also function as a table for use with medical imaging equipment.

Thus, in accordance with one aspect of the present invention, an improved patient table, preferably in the form of a wheel supported gurney, is provided. The table includes a top panel or palette for supporting a trauma patient. The top panel is extendable laterally relative to a supporting base so that it can extend into the central aperture of medical imaging equipment such as a CT scanner.

Typical gurneys now found in hospitals are wheeled so they may be easily pushed around by personnel (including small women) in a hospital or clinic. The Federal Drug Administration requires that a gurney should be able to support a 350 pound patient. The table itself typically weighs approximately 250 to 350 pounds and even with a 350 pound patient should be easy to push.

A typical gurney table is seven feet long. It has been determined that when designing a gurney in accordance with the present invention so that it includes an extendable top that can extend into the central aperature of medical imaging equipment such a CT scanner, when such a table is positioned adjacent the medical imaging equipment, a substantial portion of the top should be able to be laterally extended, e.g., as much as five feet, out from the supporting base, with the remaining portion, e.g., only two feet, of the top supported over the base. The patient on the panel is thus cantilevered relative to the table base. A particular concern, however, is that a patient extended out into the imaging equipment may become frightened, try to push against the imaging equipment and get off the table from the cantilevered end. This could easily cause the table to tip and possibly injure the patient.

Accordingly, it is another object of the present invention to provide an improved system for stabilizing the relation between a patient trauma table and the medical imaging equipment.

Another object of the present invention is to provide a system for stabilizing the table relative to the imaging equipment so that even excessive patient load can be safely controlled under emergency conditions.

Yet, other objects of the present invention are to provide such a stabilization system in which the table can be fixed relative to the frame of the imaging equipment in order to insure that there is no relative movement between the table and imaging equipment during the imaging process, and to provide such a stabilization system wherein the position of the table top relative to the frame can readily be ascertained.

The objects of the present invention are effected generally by the provision of a system for stabilizing a table having a top including a patient-supporting panel capable of being moved into a cantilevered position relative to the supporting base of the table so that a portion of the panel is disposed in an imaging position with respect to medical imaging equipment.

In the preferred embodiment of the system, the supporting table base includes a pair of vertically extendible devices such as screw jacks for raising, lowering and/or tilting the table top relative to the imaging equipment, the vertical extensible devices each preferably being controlled by a stepper motor. The supporting table base is designed to be attachable to the supporting structure of the imaging equipment to establish a fixed relation between the table and the imaging equipment that allows substantially no relative movement between them. A stabilizing device preferably includes a support arm having a roller at one end. The support arm is preferably fixed relative to the frame of the imaging equipment for incremental vertical movement by a stepper motor so that the roller is movable in and out of contact with the underside of the cantilevered end of the patient-supporting panel. For safety reasons, means, preferably in the form of a strain gauge, are coupled to the support arm for providing an indication of when to stop the stepper motor from advancing the support arm further against the table patient-supporting panel when a predetermined roller contact pressure is exceeded. A counter is provided for counting the steps provided by the stepper motor driving the support arm so that the precise position of the table top with respect to the components of the imaging equipment can be determined.

Other objects of the present invention will in part be more evident and will in part appear hereinafter. The invention accordingly comprises the apparatus possessing the construction, combination of elements and arrangement of parts exemplified in the following detailed disclosure and the scope of the application of which will be indicated in the claims.

BRIEF DESCRIPTION OF THE DRAWINGS

For a fuller understanding of the nature and objects of the present invention, reference should be had to the following detailed description taken in connection with the accompanying drawings wherein.

DETAILED DESCRIPTION OF THE DRAWINGS

Figure 1:
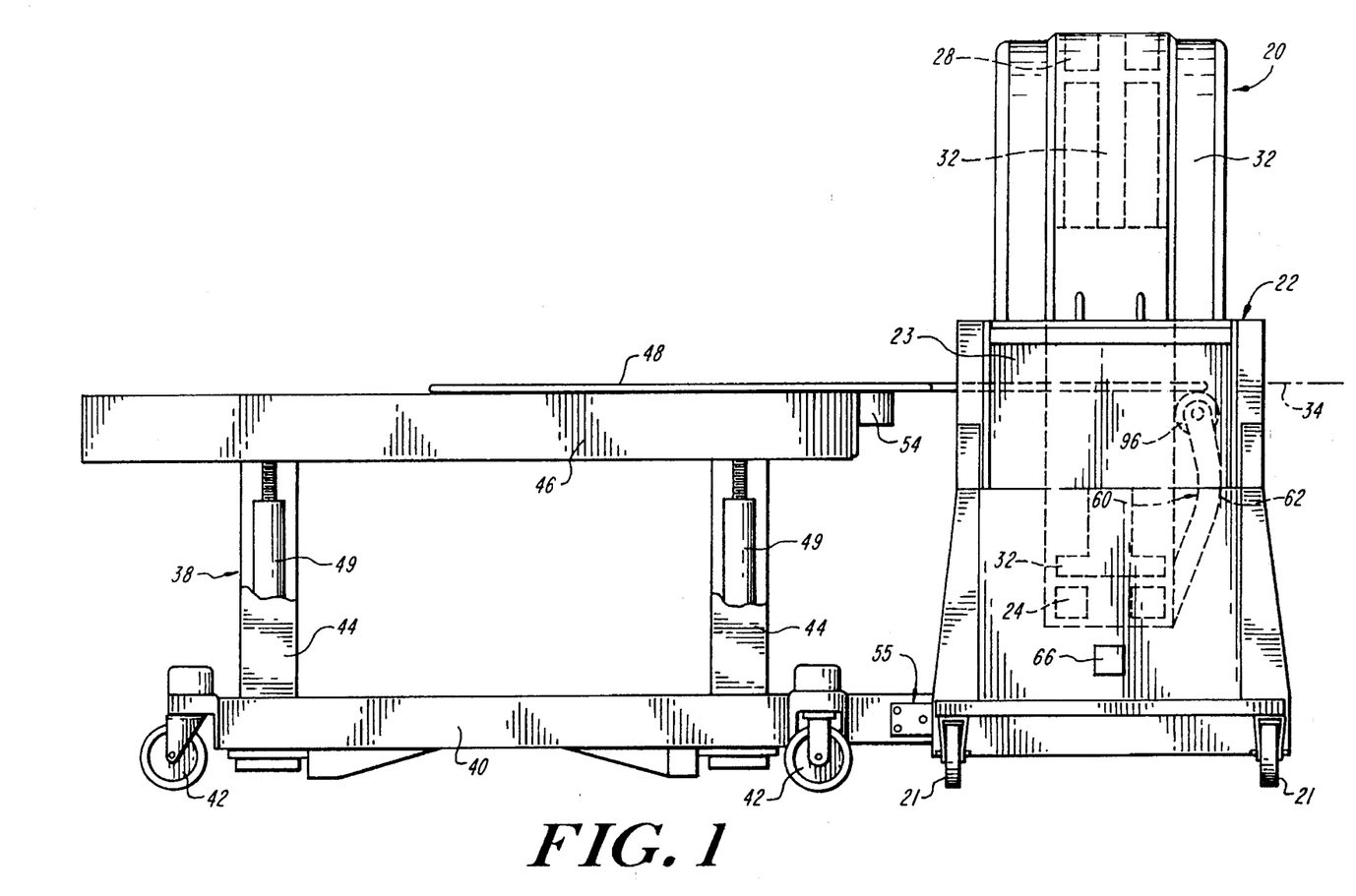
FIG. 1 is a schematic side view of structure incorporating principles of the present invention and comprising a gurney coupled to medical imaging apparatus.
Figure 2:
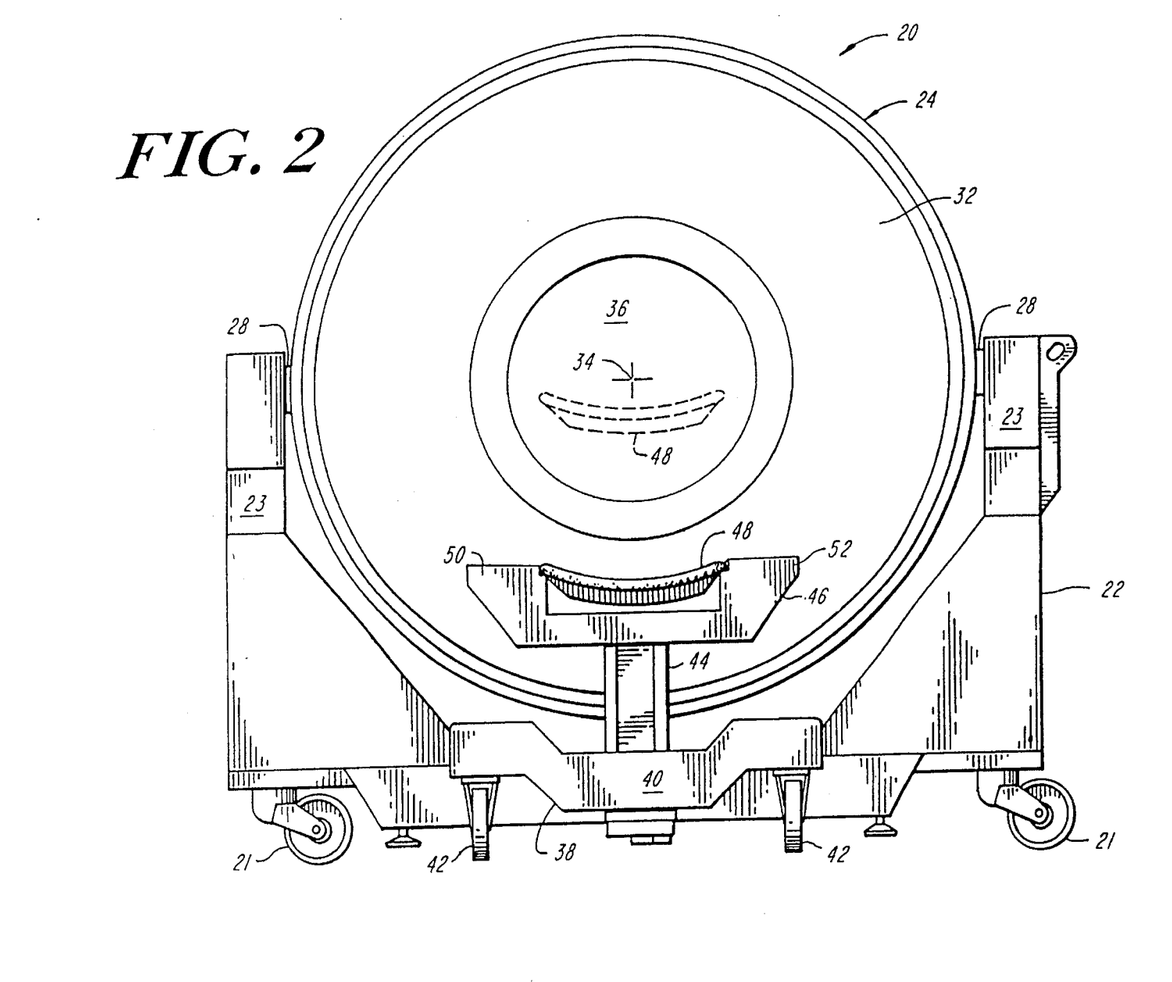
FIG. 2 is a schematic end view of the apparatus of FIG. 1.
Figure 3:
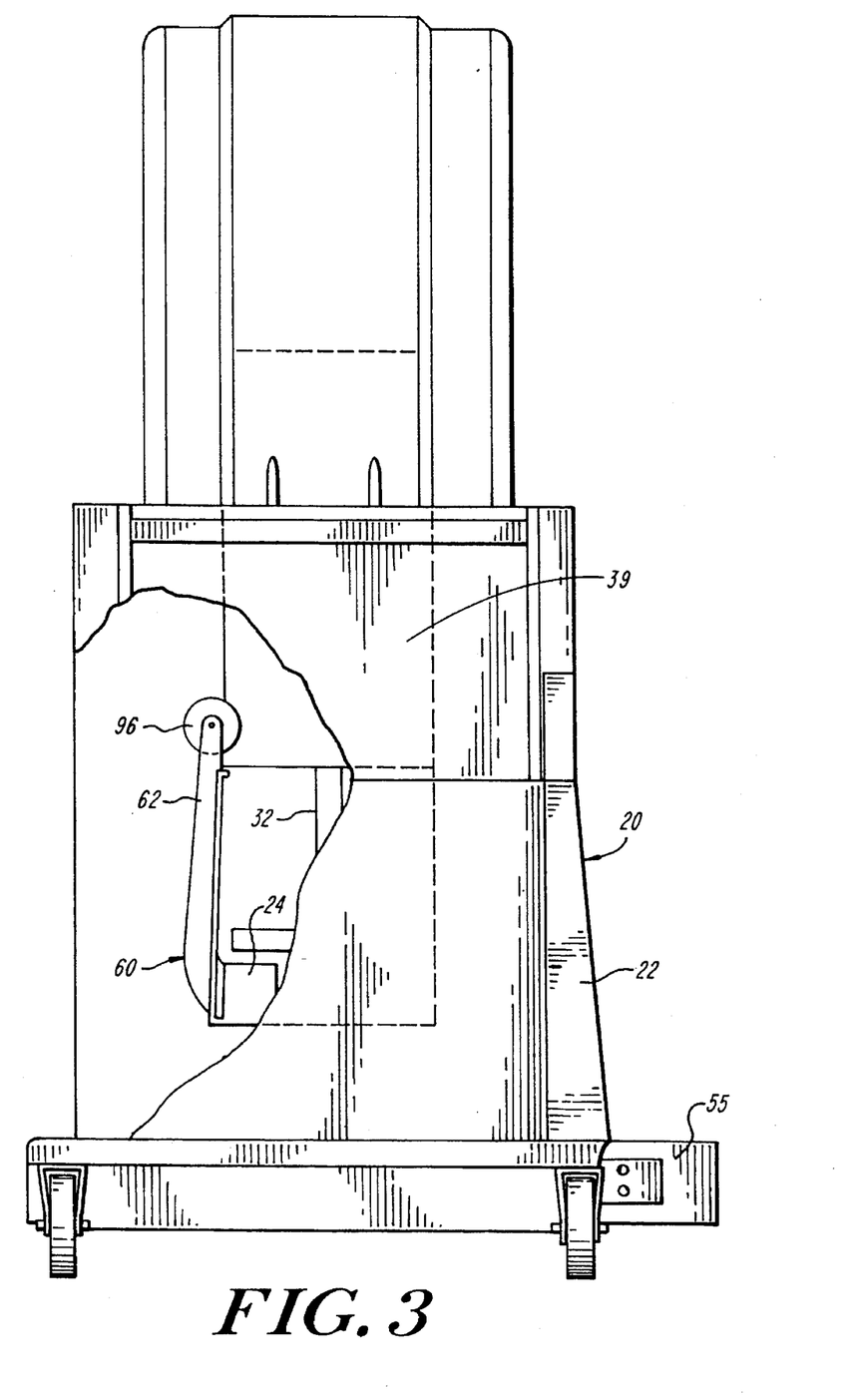
FIG. 3 is a schematic side view, partially broken away, of medical imaging apparatus of the present invention incorporating a support mechanism in accordance with the principles of the present invention.

Referring now to FIGS. 1–3 there is shown medical imaging apparatus in the form of a CT scanner. As seen in FIGS. 1 and 2, scanner preferably includes a yoke or cart 22 mounted on a plurality of wheels 21 so as to be movable or portable. Cart 22 comprises a pair of preferably rigid upright sides 23 between which is supported the CT scan gantry 20. Gantry includes rigid frame 24 which rotatably supports an annulus, shown in FIG. 2 in the form of an annular disk 32, for rotation about an axis 34. Frame 24 typically is formed as a metallic annulus or annular portion preferably of a light-weight, rigid material such as aluminum, magnesium-aluminum alloy and the like, and can be solid or hollow to minimize weight. Frame 24 is pivotally mounted on cart 22 so that the frame can be tilted about a center line or diametrical axis defined by a pair of pivots 28 (shown in FIG. 2). As best seen in FIG. 2, each of pivots 28 is fixed to frame 24 for pivotal movement therewith and extends into a corresponding bearing surface (not shown) on a respective one of sides 23 of the cart so that frame 24 can be pivoted about the pivot pins 28. In addition the pivot pins, and thus gantry 20, are mounted to the cart so that the entire gantry can be moved in translation backward and forward relative to sides 23 and parallel to the rotation axis 34. The mechanism for accomplishing the translation is not shown in the drawings, but is described in detail in copending U.S. patent application Ser. No. 08/193,562 filed in the name of Gilbert W. McKenna and assigned to the current assignee. Frame 24 is restrained from rotation in its own plane by the coupling between pivots 28 and the sides 23 of cart 22.

As best seen in FIG. 2, the annular disk 32, is rotatably mounted within frame 24, by bearings, or preferably by suitable wheels (such as described in co-pending U.S. patent application Ser. No. 08/193,783 filed in the name of Gilbert W. McKenna and assigned to the current assignee), neither of which is shown, for rotation with respect to the frame about axis 34 of rotation that extends perpendicularly through central aperture 36 of disk 32. Central aperture 36 preferably is dimensioned so that the body of a patient reposed on the top of a patient table can be inserted therethrough.

An X-ray source (not shown) for defining substantially a point source of X-rays is positioned on disk 32 in a well known manner so as to direct a beam of X-rays across aperture 36 substantially along paths disposed within a common plane normal to axis 34, i.e., defining the scanning plane. Similarly, in the case of third generation machines an X-ray detector array (also not shown) is mounted on disk 32, diametrically opposite the source, so as to detect X-rays emitted by the X-ray source after those rays have traversed aperture 36 along the paths of the rotation plane. Other well-known components (not shown), such as a high voltage supply for providing the necessary power to the X-ray source during a scan, can be supported by the disk 32. See, for example, co-pending U.S. patent application Ser. No. 08/193,696, filed in the names of Gilbert W. McKenna and Ronald Swain and assigned to the present assignee. Means for driving disk 32 in rotation are also included but, in the interest of brevity are also not shown, being wholly conventional and described in detail in, for example, U.S. Pat. No. 4,928,283. To protect and conceal the array of components distributed around the disk and frame of gantry 20, a skin or cover 39 (only a portion of which is shown in FIGS. 1 and 3) of an X-ray transparent material such as a light-opaque high molecular weight polymer is positioned by a plurality of fasteners to the gantry assembly.

FIGS. 1 and 2 also show a separate, movable patient table or gurney 38 modified in accordance with one aspect of the present invention. The gurney 38 includes a supporting base generally comprising a horizontal base member 40 supported on a plurality of wheels 42 in combination with upright support members 44 supported on base member 40 at the lower ends thereof. Members 44 serve to support at their upper extremities elongated horizontal table top 46. In accordance with one aspect of the present invention, the table top 46 includes means for suspending a patient so that he or she is cantilevered relative to the base member 40 in order to extend the patient into the aperture 36 of the disk. In a preferred embodiment, the means includes an elongated patient palette or panel 48 positioned on top 46, panel 48 being slidably captured along its long edges within two laterally extending, grooved side or rail members 50 and 52 (seen in FIG. 2) mounted along corresponding sides of table top 46. Means, in the form of a conventional extension drive apparatus 54 (seen in FIG. 1 ) such as a stepping motor driving a belt device of a known configuration and therefore only shown only in block form, is mounted relative to top 46 and connected to panel 48 in a well known manner for driving the latter so that at least a portion of a patient lying on the panel can be moved relative to the base member 40 in and out of aperture 36 of the gantry 20.

As best seen in FIG. 2, panel 48 is preferably formed as a transversely curved member the side edges of which are slidably engaged by the grooves in rail members 50 and 52, although flat panels can be used. At least that portion of panel 48 intended to be extendible into aperture 36 is preferably X-ray transparent.

In a preferred embodiment, upright support members 44 may comprise telescoping tubes or similar means by which the height of the foot and head ends of table top 46 above the floor can be readily and independently adjusted by conventional table height adjustment means 49, preferably in the form of a pair of vertically extendible devices such as screw jacks for raising, lowering and/or tilting the table top relative to the imaging equipment, as shown in FIG. 1 in block form only. Such table height adjustment means facilitates positioning a patient at the center of the tomography apparatus, as seen in FIG. 1 wherein the dotted lines indicate the extension of panel 48 into aperture 36, and in FIG. 2 where the dotted outline within aperture 36 illustrates the position of panel 48 when table top 46 is in an elevated and extended (cantilevered) position.

As seen in FIG. 1, table base 40 is designed to be fixed relative to the gantry 20, and particularly to cart 22 which supports frame 24 and disk 32 so as to establish a releasably fixed relation between gurney 38 and gantry 20 so as to prevent relative longitudinal movement between them. To this end, mounted at one end of table base 40 and on the base of cart 22 at matching heights above floor level are respective mating parts of a positive-locking, quick-release mechanism or latch 55 of a well known type, such as any of the several devices described and shown by N. P Chironis, *Mechanisms and Mechanical Devices Handbook*, McGraw Hill, Inc (1991), pp. 400–409.

Figure 4:
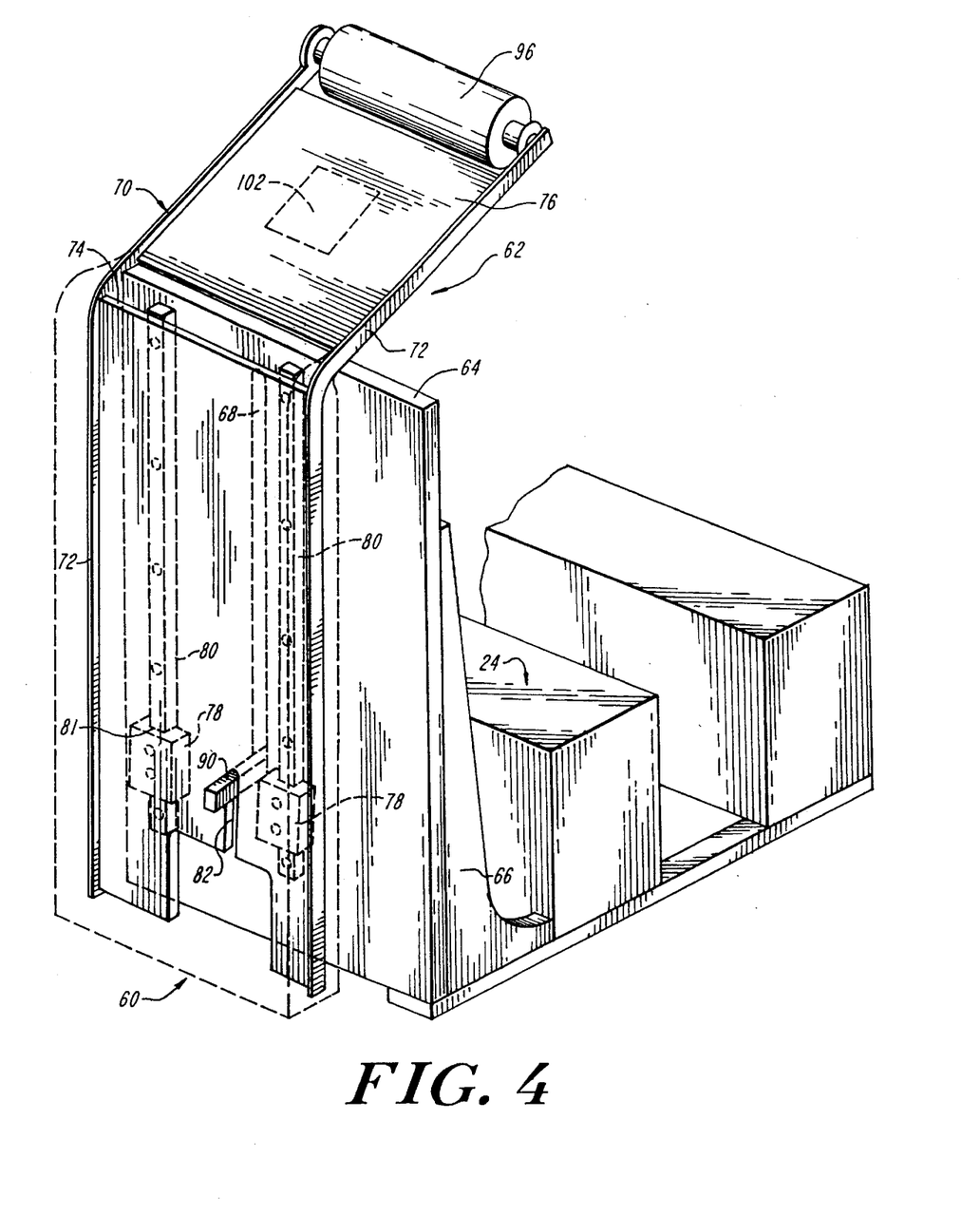
FIGS. 4 and 5 are perspective views, partially broken away, showing the stabilization system of the present invention.

As best seen in FIGS. 1, 3, 4 and 5, the present invention also includes means, generally indicated at 60, for supporting and stabilizing the portion of panel 48 when table base 40 and cart 22 are releasably locked together and that portion of panel 48 is extended into aperture 36. Such support means is preferably provided in the form of elongated metal support arm assembly, generally indicated at 62. The assembly 62 is slidably fixed relative to the frame 24 (as best seen in FIG. 4), within the cover 39 (as shown in FIGS. 1 and 3) so that it is positioned on the side of the gantry 20 opposite the side bearing the mating portion of latch 55 (of FIG. 1) and thus opposite the side of the gantry receiving the panel 48.

Figure 5:
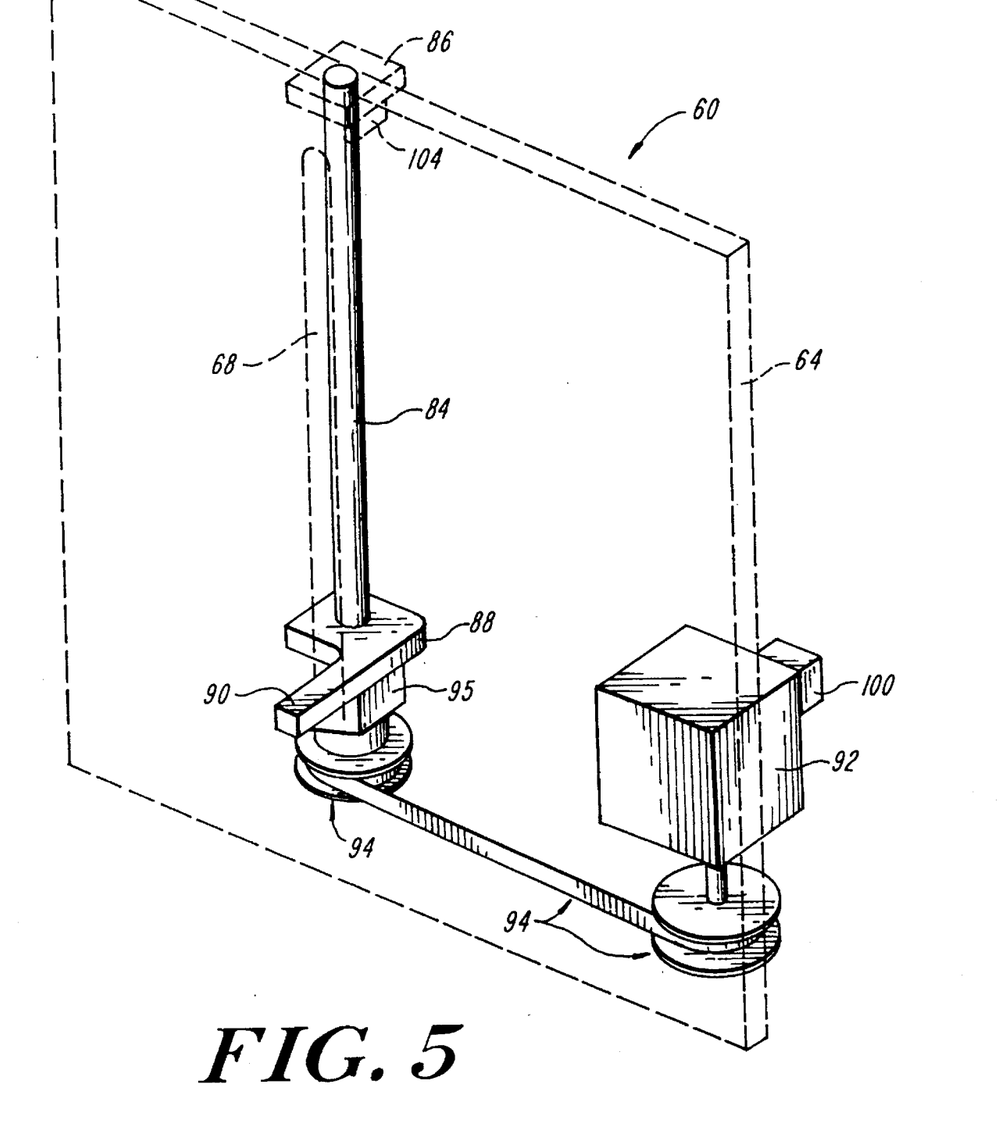

Describing the support means 60 in greater detail, referring to FIGS. 4 and 5, the support arm assembly 62 is supported by a support plate 64, which in turn is secured to the frame 24 by gussets 66 (one being shown in FIG. 4), for supporting the components of the support means 60. The plate 64 is provided with a vertically oriented slot 68 which is longer than the anticipated range of vertical movement of the support arm 62 as will become more apparent hereinafter. The components of the preferred support arm assembly 62 positioned in front of the support plate 64 (from the perspective of FIGS. 4 and 5) are illustrated in FIG. 4, while those components positioned behind the support plate are shown in FIG. 5.

Referring to FIG. 4, a support arm assembly 62 is mounted for vertical movement relative to the support plate 64, and thus the frame 24. The support arm assembly 62 includes a frame 70 comprising at least a pair of parallel, bent arms 72, a bottom portion of which extends vertically for supporting the vertical panel 74 therebetween, and a top portion of which extends at an angle to the vertical for supporting the diagonal panel 76. A pair of blocks 78 are secured to the back of the vertical panel 74 so as to be disposed between the panel and the support plate. The blocks are provided with slots 81 which are formed to respectively cooperate with a pair of linear ways 80, which in turn are mounted on the front side of the support plate 64 so as to be vertically oriented and parallel to one another, so as to limit movement of the assembly to an up or down motion in the vertical direction. As seen in FIG. 4, the bottom edge of the vertical panel is provided with a vertical slot 82.

The components for moving the assembly 62 in a vertical direction are shown in FIG. 5. A ball screw 84 is supported at each end in a journal 86 (only one being shown in FIG. 5). The ball screw 84 is supported so that it is restrained from movement axially, but freely rotates about its longitudinal axis. A ball nut assembly, generally shown at 88, includes a finger 90 (seen in FIGS. 4 and 5) which as shown in FIG. 4 extends through the slot 68 of the support plate 64 and slot 82 of the vertical panel 74 of the assembly 62 so as to support the assembly 62. As seen in FIG. 5, the ball nut assembly 88 is rotatably supported on the ball screw 84, but is restrained from rotational movement (because finger 90 extends through the slot 68) to axial movement along the axis of the ball screw 84 when the ball screw is rotatably driven within the journals 86 about its axis. The ball screw is rotatably driven by means, preferably in the form of a stepping motor 92, coupled through a belt driven pulley system 94 to the ball screw 84 so that rotation of the motor 92 in one direction causes the ball screw 84 to rotate (within the journals 86) in one direction and the ball nut to travel up the ball screw pushing the support arm assembly 62 with the finger 90, while rotation of the motor 92 in the opposite direction causes the ball screw 84 to rotate in an opposite direction and the ball nut to travel down the ball screw, lowering the support arm assembly 62 as the finger moves down the slot 68 of the support plate 64. For safety reasons, a slip clutch 95 (seen in FIG. 5) of a well known type, is provided for the full stroke of the ball nut assembly 88 so that the ball nut assembly 88 will slip relative to the ball screw 84 should a vertical force be applied to the support arm assembly 62 in excess of a predetermined amount, thus, preventing injury to any person when the ball nut assembly is being raised or lowered.

The support arm assembly 62 is dimensioned and positioned so that it is moveable into contact with the underside of panel 48 when the latter is extended into its cantilevered position. Mounted on the upper end of support arm assembly 62 are means, such as wheel or roller 96, for providing a rolling contact between the assembly 62 and panel 48.

Referring to FIG. 1, because the floor on which gurney 38 and cart 22 are located can be uneven, notwithstanding that the gurney and cart may be connected to one another near wheels 42, panel 48 when extended may be positioned at a different location than one might expect. Further, the weight of a patient on extended panel 48 may cause the panel to bend. Thus, as seen in FIG. 5, means, shown generally as counter 100, electrically connected to stepper motor 92, is provided for up-down counting the steps provided by operation of stepper-motor 92, thereby permitting one to ascertain the exact position of extended panel 48 relative to the frame 24 and the imaging components of gantry 20 as seen in FIG. 1. For safety reasons, stress or torque-measuring means 102 shown in FIG. 4, such as a spring-scale, strain gauge, Bourdon tube or the like is so attached and positioned with respect to the underside of the diagonal panel 76 so as to measure the build-up of compressive stress so that when the stress exceeds a predetermined threshold, e.g., six psi pressure, a signal is provided to stop the operation of stepper motor 92. This is helpful when moving the roller 96 into contact with the underside of panel 48 so as to prevent excess strain on the support arm assembly. Similarly, if an obstruction such as a person's finger is caught between roller 96 and panel 48 when moving the support arm assembly up, stepper motor 92 will also turn off when the contact pressure reaches the threshold level. Thus, there can not be a great amount of force applied to the person's finger thereby preventing serious harm to the person.

Manually operable controls (not shown) are preferably provided for controlling the direction and speed of stepper motor 92. As seen in FIG. 5, suitable switches 104 (one being shown in FIG. 5) can be positioned at the two desired end positions of the ball screw 84 (e.g., adjacent journals 86) so that the finger 90 of the assembly will not travel beyond predetermined extreme positions. The switches 104 are suitably connected to the stepper motor 92 so that the motor will stop when the nut assembly 88 moves into position to close one of the switches.

In preparation for a CAT scan, cart 22 and gurney 38 would be wheeled into position so that the components of latch 55 can be releasably locked to one another, fixing the position of the gantry 20 and gurney relative to one another as best seen in FIG. 1. Table top 46 is then elevated to the desired height for centering panel 48 with respect to aperture 36 in gantry 20. Then, panel 48, carrying a subject patient would be slidably moved into the inner, annular aperture 36 to position the patient properly with respect to the gantry of the CAT scan mechanism as seen in FIG. 1. Regardless of the weight of the patient or the relative extension of panel 48 into aperture 36, the position of the portion of panel 48 extended within aperture 36, and consequently the position of the patient relative to the tomography apparatus, is maintained by the support provided by the support arm assembly 62 and roller 96, and the position of the panel and patient can readily be ascertained by examination of the read-out from counter 100 (seen in FIG. 5). Once the patient is thus initially positioned relative to the tomography apparatus, further movement of the patient or patient table is unnecessary with the apparatus of this invention, because gantry 20 generally includes means providing controlled lateral translation of the gantry 20 along the rotation axis (as described in co-pending application U.S. Ser. No. 08/193, 562, mentioned above) in order to properly position the gantry relative to the patient so as to generate the X-ray data needed for imaging. In one embodiment of this invention, therefore, X-ray imaging is performed step-wise in conjunction with incremental, precisely measured, discrete displacements of the gantry assembly with respect to the patient, which displacements are effected by briefly and repeatedly activating the gantry displacement system. In an alterative embodiment, X-ray imaging can also be carried out continuously as a helical scan by activating the gantry displacement mechanism for gradual, continuous and precisely measured lateral displacement of the gantry assembly while the tomography system is in operation.

The system thus described provides an improved patient table which functions both as a gurney and a table for use with large medical imaging equipment. The support means 60 provides stabilization of the cantilevered table during imaging.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. A table for supporting a patient in a reposed position, said table comprising:

a base supported on wheels;

a planar top for supporting the patient in a reposed position and supported by and capable of being moved relative to said base so that a portion of patient can be cantilevered relative to the base;

support means for supporting the cantilevered portion of said planar top when said patient is cantilevered relative to said base; and means for controllably moving said support means into and out of supporting contact with the cantilevered portion of said planar top.

2. In combination:

a medical imaging system for forming an internal image of a portion of a patient disposed in an imaging position;

a patient table comprising a base supported on wheels, and a planar top for supporting the patient and capable of being moved relative to said base so that a portion of patient can be cantilevered relative to the base and positioned in said imaging position;

Support means for supporting the cantilevered portion of said planar top when said patient is disposed in said imaging position; and means for controllably moving said support means into and out of supporting contact with the cantilevered portion of said planar top.

3. The combination according to claim 2, further including means for securing said table to said imaging system.

4. The combination according to claim 2, further including means for stabilizing said table relative to said imaging system when said planar top is cantilevered relative to said base with said patient in said imaging position.

5. In combination with medical imaging equipment and a patient table having a base and an elongated, substantially planar top for supporting a patient and supported by and capable of being cantilevered relative to said base so that a portion thereof is disposed in an imaging position with respect to said imaging equipment, a system for stabilizing said table when said table top portion is disposed in said imaging position with respect to said imaging equipment, said system comprising:

support means, fixed relative to said imaging equipment, for supporting said portion of said top when the latter is disposed in said imaging position; and means for moving said support means into and out of supporting contact with said top when the latter is disposed in said imaging position.

6. A stabilizing system as set forth in claim 5, further including means for laterally moving said top, substantially in the plane of said top, with respect to said base into and out of said imaging position.

7. A stabilizing system as set forth in claim 5, further including means for vertically moving the top relative to the base substantially normally to the plane.

8. A stabilizing system as set forth in claim 5, wherein said imaging equipment is an X-ray tomography system including a gantry including a frame and a disk mounted in the frame for rotation about a rotation axis, and wherein said portion of said top extends into said aperture when in said imaging position.

9. A stabilizing system as set forth in claim 5, further including means for determining the contact force between the support means and said portion of said top.

10. A stabilizing system as set forth in claim 9, further including means for arresting said movement of said support means when said contact force exceeds a predetermined limit.

11. A stabilizing system as set forth in claim 10, wherein said predetermined limit is not substantially greater than about 6 lbs.

12. A stabilizing system as set forth in claim 9, wherein said means for determining said contact force comprises transducer means for providing an output signal representative of said contact force.

13. A stabilizing system as set forth in claim 12, wherein said means for arresting comprises means for controlling said means for moving said support means in accordance with said output signal.

14. A stabilizing system as set forth in claim 5, wherein said support means includes at least one roller mounted on said support means so as to provide rolling contact between said portion of said top and said support means.

15. A stabilizing system as set forth in claim 5, wherein said means for moving said support means comprises a ball nut assembly contacting said support means and axially movable along a ball screw, and driver means mounted on said equipment for driving said ball screw so as to axially move said ball nut assembly.

16. A stabilizing system as set forth in claim 15, wherein said drive means comprise a stepping motor.

17. A stabilizing system as set forth in claim 16, including counter means for counting each increment stepped by said stepping motor so that the relative position of said portion of said top to said medical imaging equipment can be ascertained when said contact is established.

18. A stabilizing system as set forth in claim 16, wherein said imaging equipment includes imaging components disposed on a gantry, said system further including means for releasably locking one end of said table to said imaging equipment to establish a fixed spatial relation between the imaging components and said portion of said top when the latter is disposed in said imaging position.

19. A stabilizing system as set forth in claim 5, further including drive means, mounted on said top, for moving said top into said cantilevered position.

20. A stabilizing system as set forth in claim 19, wherein said drive means comprises a stepping motor.

* * * * *